United States Patent [19]

Schmailzl

[11] Patent Number: 5,644,060

[45] Date of Patent: Jul. 1, 1997

[54] PROCESS FOR THE PREPARATION OF 1-OXA-3,8-DIAZA-4-OXOSPIRO[4.5]DECANE COMPOUNDS

[75] Inventor: Georg Schmailzl, Gersthofen, Germany

[73] Assignee: Hoechst Atkiengesellschaft, Frankfurt, Germany

[21] Appl. No.: 333,239

[22] Filed: Nov. 2, 1994

Related U.S. Application Data

[63] Continuation of Ser. No. 81,867, Jun. 23, 1993, abandoned, which is a continuation of Ser. No. 738,101, Jul. 30, 1991, abandoned.

[30] Foreign Application Priority Data

Aug. 1, 1990 [DE] Germany .................. 40 24 415.6

[51] Int. Cl.$^6$ ................................. C07D 498/10
[52] U.S. Cl. ................................................. 546/19
[58] Field of Search ..................................... 546/19

[56] References Cited

U.S. PATENT DOCUMENTS

| | | | |
|---|---|---|---|
| 4,110,334 | 8/1978 | Mayer et al. | 546/19 |
| 4,408,051 | 10/1983 | Hinsken et al. | 546/19 |
| 4,689,416 | 8/1987 | Ertl et al. | 546/19 |

FOREIGN PATENT DOCUMENTS

| | | |
|---|---|---|
| 0 208 263 | 1/1987 | European Pat. Off. . |
| 3 149 453 | 8/1982 | Germany . |
| 3 523 679 | 1/1986 | Germany . |

*Primary Examiner*—Ba K. Trinh
*Attorney, Agent, or Firm*—Connolly & Hutz

[57] ABSTRACT

The invention relates to an environmentally friendly process for the preparation of compounds of the formula below

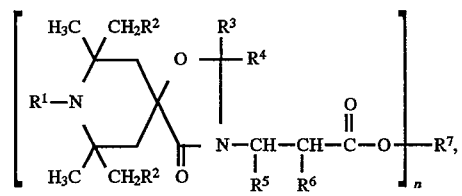

in which $R^1$ and $R^2$ are preferably H or alkyl, $R^3$ and $R^4$ are preferably alkyl or cycloalkyl, $R^5$ and $R^6$ are preferably hydrogen or methyl and $R^7$ is in particular alkyl. In the process, the additional use of a phase transfer catalyst can be dispensed with without loss in yield.

15 Claims, No Drawings

PROCESS FOR THE PREPARATION OF 1-OXA-3,8-DIAZA-4-OXOSPIRO[4.5]DECANE COMPOUNDS

This application is a continuation of application Ser. No. 08/081,867 filed Jun. 23, 1993, now abandoned, which was a continuation of Ser. No. 07/738,101, filed Jul. 30, 1991, now abandoned.

The invention relates to a process for the preparation of 1-oxa-3,8-diaza-4-oxospiro[4.5]decane compounds, which can be used as light stabilizers for polymers or as intermediates in the preparation of plastic additives. Compounds of the formula

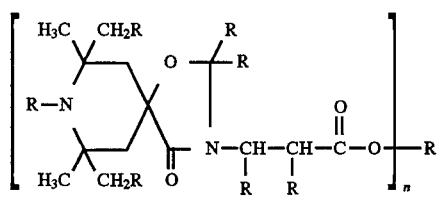

are known (cf. DE 3,149,453).

However, the process for their preparation described in DE 3,149,453 is complicated, since the reaction medium has to be changed several times during the reaction, thus requiring additional extractions and distillations.

DE 3,524,543 describes an improved preparation process for these compounds which comprises carrying out the synthesis in an aromatic hydrocarbon which is liquid at room temperature and, in addition to a basic catalyst, using a phase transfer catalyst.

It is true that the addition of a phase transfer catalyst described in DE 3,524,543 results in much more rapid and more complete conversion, but it has the disadvantageous side effect of causing more pollution, since the phase transfer catalyst enters the waste water when the reaction mixture is worked up. The use of phase transfer catalysts means, in the favorable case—when polyethylene glycol dialkyl ethers are used—an increase in the organic load in the waste water and thus increased pollution. If the quaternary ammonium or phosphonium halides described in DE 3,524,543 as particularly effective are used as phase transfer catalysts, this not only increases the organic load in the waste water but makes it even impossible to introduce the waste water into a biological treatment plant, since quaternary ammonium and phosphonium salts have a bactericidal effect and cannot be processed in a biological treatment plant. Therefore, the waste water has to be disposed of as special waste in a complicated manner.

The object was therefore to find a process which provides the compounds mentioned at the beginning in very short reaction times and very high yields without having the disadvantages known from the prior art of a too low compatibility with the environment and the resulting complicated waste water disposal.

This is achieved according to the invention by using an aromatic hydrocarbon which is liquid at room temperature as the solvent and a compound of the formula X

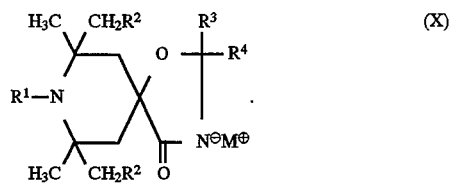

as the only catalyst when preparing the compounds mentioned.

Accordingly, the present invention relate to a process for the preparation of 1-oxa-3,8-diaza-4-oxospiro[4.5]-decane compounds of the formula I

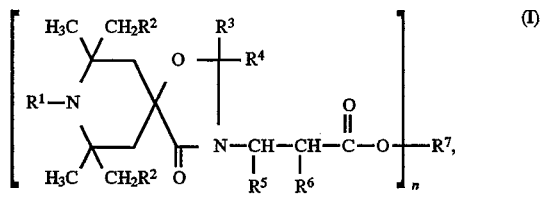

in which n is an integer from 1 to 4, $R^1$ is hydrogen, $C_1$–$C_4$-alkyl, benzyl, allyl, $C_2$–$C_{30}$-alkanoyl, $C_3$–$C_{20}$-alkenoyl, $C_7$–$C_{11}$-aroyl, $C_8$–$C_{14}$-arylalkanoyl or $C_8$–$C_{20}$-alkylaryl, $R^2$ is hydrogen or $C_1$–$C_4$-alkyl, $R^3$ is hydrogen, $C_1$–$C_8$-alkyl, $C_5$–$C_{12}$-cycloalkyl, a phenyl or naphthyl group which can be substituted by chlorine or $C_1$–$C_4$-alkyl, or a $C_7$–$C_{12}$-phenylalkyl group which is unsubstituted or substituted by $C_1$–$C_4$-alkyl, $R^4$ is hydrogen, $C_1$–$C_4$-alkyl, $C_5$–$C_{12}$-cycloalkyl, $C_1$–$C_3$-alkenyl which is substituted by —COOH, carb-$C_1$–$C_4$-alkoxy or carbamoyl, a phenyl, naphthyl or pyridyl group which can be substituted by $C_1$–$C_4$-alkoxy or $C_1$–$C_4$-alkyl, or a $C_7$–$C_{12}$-phenylalkyl group which can be substituted by $C_1$–$C_4$-alkyl, or $R^3$ and $R^4$, together with the carbon atom linking them, are a cycloalkyl group which can be substituted by one to four $C_1$–$C_4$-alkyl groups, or a radical of the formula II

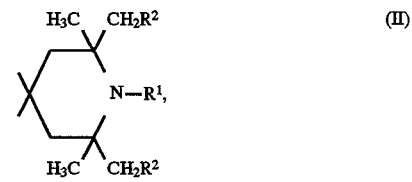

where $R^1$ and $R^2$ have the abovementioned meaning, $R^5$ is hydrogen, methyl, phenyl or carb-$C_1$–$C_{21}$-alkoxy, $R^6$ is hydrogen or methyl, $R^7$ is, if n is 1, hydrogen, $C_1$–$C_{21}$-alkyl, $C_2$–$C_{22}$-alkenyl, $C_7$–$C_{18}$-phenylalkyl, $C_5$–$C_{12}$-cycloalkyl, phenyl, naphthyl, $C_7$–$C_{18}$-alkylphenyl, a radical of the formula

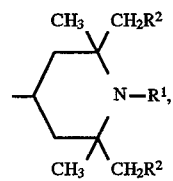

where $R^1$ and $R^2$ have the above meaning, $C_2$–$C_{20}$-alkyl which is interrupted by —O— or $$-\underset{\underset{R^8}{|}}{N}-$$

and/or substituted by a radical of the formula III (formula III showing piperidine ring with $H_3C$, $CH_2R^2$ substituents, $R^1-N$, ring with O, $R^4$, and $-N-CH-CH-C(=O)-O-$ with $R^5$, $R^6$)

or by $C_1-C_{21}$-alkylcarboxyl, where $R^1$, $R^2$, $R^3$, $R^4$, $R^5$ and $R^6$ have the above meaning and $R^8$ is hydrogen or $C_1-C_{10}$-alkyl, $R^7$ is, if n is 2, straight-chain or branched $C_1-C_{30}$-alkylene, $C_2-C_{30}$-alkenylene, phenyldialkylene, it being possible for these radicals to be interrupted by —O— or $$-\underset{\underset{R^8}{|}}{N}-,$$

where $R^8$ has the above meaning, $R^7$ is, if n is 3 or 4, a radical of the formulae IV, V, VI or VII $$-CH_2-\underset{|}{CH}-CH_2-, \quad (IV)$$

$$C_2H_5-\underset{\underset{CH_2}{|}}{\overset{\overset{CH_2}{|}}{C}}-CH_2-, \quad (V)$$

$$-CH_2CH_2-\underset{\underset{CH_2CH_2-}{|}}{N}-CH_2-CH_2-, \quad (VI)$$

$$-CH_2-\underset{\underset{CH_2}{|}}{\overset{\overset{CH_2}{|}}{C}}-CH_2-, \quad (VII)$$

by reaction of a compound of the formula VIII (formula VIII, piperidine ring with $R^1-N$, $H_3C$, $CH_2R^2$ substituents, $R^3$, $R^4$, O, NH)

with a compound of the formula IX $$\left[\underset{\underset{R^5}{|}}{CH}=\underset{\underset{R^6}{|}}{C}-\overset{\overset{O}{\|}}{C}-O\right]_n R^7, \quad (IX)$$

where n, $R^1$, $R^2$, $R^3$, $R^4$, $R^5$, $R^6$ and $R^7$ have the above-mentioned meaning, an inert solvent at a temperature of 30° to 150° C. and in the presence of a catalyst, which comprises carrying out the reaction in the presence of 1 to 10 mol %, relative to the compound VIII, of a catalyst of the formula (X)

(formula X, similar piperidine ring structure with $N^\ominus M^\oplus$)

where $R^1$, $R^2$, $R^3$ and $R^4$ have the abovementioned meaning and M is an alkali metal, in an aromatic hydrocarbon which is liquid at room temperature.

$R^1$ is preferably hydrogen, $C_1-C_4$-alkyl, $C_2-C_{18}$-alkanoyl, for example methyl, ethyl, propyl, butyl, acetyl, propionyl, butyryl, lauroyl, stearoyl, particularly preferably hydrogen or one of the acid radicals mentioned. $R^1$ is in particular hydrogen.

$R^2$ is preferably hydrogen or $C_1-C_4$-alkyl, for example methyl, ethyl, propyl, butyl. R2 is in particular hydrogen.

$R^3$ and $R^4$, independently of one another, are $C_1-C_{18}$-alkyl, $C_5-C_{12}$-cycloalkyl or phenyl, for example ethyl, butyl, octyl, lauryl, stearyl, cyclohexyl, cyclodecyl, particularly preferably $C_1-C_7$-alkyl. $R^3$ and $R^4$ are in particular $C_1-C_4$-alkyl, for example methyl.

$R^3$ and $R^4$, together with the carbon atom linking them, are preferably $C_5-C_{12}$-cycloalkylene, particularly preferably $C_5-$ or $C_{12}$-cycloalkylene, in particular cyclododecylene.

$R^5$ is preferably hydrogen, methyl or phenyl, particularly preferably hydrogen.

$R^6$ is preferably hydrogen or methyl. $R^5$ is in particular hydrogen.

$R^7$ is preferably $C_1-C_{21}$-alkyl, straight-chain or branched $C_1-C_{30}$-alkylene, for example methyl, butyl, octyl, lauryl, stearyl, ethylene, butylene, hexylene, particularly preferably $C_1-C_5$-alkyl. $R^7$ is in particular $C_{12}-C_{14}$-alkyl, for example lauryl.

The starting compounds of the formulae VIII and IX are known and their preparation is described in the literature (for example DE 3,149,453 and DE 2,606,026).

Examples of suitable compounds of the formula VIII are
2-butyl-7,7,9,9-tetramethyl-1-oxa-3,8-diaza-4-oxospiro-[4.5]decane
2-isobutyl-7,7,9,9-tetramethyl-1-oxa-3,8-diaza-4-oxo-spiro[4.5]decane
2-pentyl-7,7,9,9-tetramethyl-1-oxa-3,8-diaza-4-oxospiro-[4.5]decane
2-isopentyl-7,7,9,9-tetramethyl-1-oxa-3,8-diaza-4-oxo-spiro[4.5]decane
2-hexyl-7,7,9,9-tetramethyl-1-oxa-3,8-diaza-4-oxo-spiro[4.5]decane
2-heptyl-7,7,9,9-tetramethyl-1-oxa-3,8-diaza-4-oxospiro-[4.5]decane
2-isoheptyl-7,7,9,9-tetramethyl-1-oxa-3,8-diaza-4-oxo-spiro[4.5]decane
2-nonyl-7,7,9,9-tetramethyl-1-oxa-3,8-diaza-4-oxospiro-[4.5]decane
2-isononyl-7,7,9,9-tetramethyl-1-oxa-3,8-diaza-4-oxo-spiro[4.5]decane
2-undecyl-7,7,9,9-tetramethyl-1-oxa-3,8-diaza-4-oxospiro-[4.5]decane
2-phenyl-7,7,9,9-tetramethyl-1-oxa-3,8-diaza-4-oxospiro-[4.5]decane
2-(4-chlorophenyl)-7,7,9,9-tetramethyl-1-oxa-3,8-diaza-4-oxospiro[4.5]decane 2-ethyl-2,7,7,9,9-pentamethyl-1-oxa-3,8-diaza-4-oxospiro-[4.5]decane
2-propyl-2,7,7,9,9-pentamethyl-1-oxa-3,8-diaza-4-oxospiro[4.5]decane
2-isopropyl-2,7,7,9,9-pentamethyl-1-oxa-3,8-diaza-4-oxospiro[4.5]decane
2-butyl-2,7,7,9,9-pentamethyl-1-oxa-3,8-diaza-4-oxospiro-[4.5]decane
2-isobutyl-2,7,7,9,9-pentamethyl-1-oxa-3,8-diaza-4-oxospiro[4.5]decane
2-pentyl-2,7,7,9,9-pentamethyl-1-oxa-3,8-diaza-4-oxospiro[4.5]decane
2-hexyl-2,7,7,9,9-pentamethyl-1-oxa-3,8-diaza-4-oxospiro[-4.5]decane
2-nonyl-2,7,7,9,9-pentamethyl-1-oxa-3,8-diaza-4-oxospiro-[4.5]decane
2,2,7,7,9,9-hexamethyl-1-oxa-3,8-diaza-4-oxospiro[4.5]-decane
2,2,7,7,8,9,9-heptamethyl-1-oxa-3,8-diaza-4-oxospiro-[4.5]decane
2,2-diethyl-7,7,9,9-tetramethyl-1-oxa-3,8-diaza-4-oxo-spiro[4.5]decane
2,2-dipropyl-7,7,9,9-tetramethyl-1-oxa-3,8-diaza-4-oxospiro[4.5]decane
2,2-dibutyl-7,7,9,9-tetramethyl-1-oxa-3,8-diaza-4-oxospiro[4.5]decane
2-ethyl-2-pentyl-7,7,9,9-tetramethyl-1-oxa-3,8-diaza-4-oxospiro[4.5]decane
2,2-dibenzyl-7,7,9,9-tetramethyl-1-oxa-3,8-diaza-4-oxospiro[4.5]decane
2,2,4,4-tetramethyl-7-oxa-3,13-diaza-14-oxodispiro-[5.1.4.2]tetradecane
2,2,4,4-tetramethyl-7-oxa-3,14-diaza-15-oxodispiro-[5.1.5.2]pentadecane
2,2,4,4-tetramethyl-7-oxa-3,20-diaza-21-oxodispiro-[5.1.11.2]heneicosane
2,2,7,7,9,9-hexamethyl-1-oxa-3,8-diaza-4-oxo-8-acetylspiro[4.5]decane
2,2,4,4-tetramethyl-7-oxa-3,14-diaza-15-oxo-3-acetyl-dispiro[5.1.5.2]pentadecane
2,2,4,4-tetramethyl-7-oxa-3,20-diaza-21-oxo-3-acetyl-dispiro[5.1.11.2]heneicosane Examples of suitable compounds of the formula IX are
methyl acrylate
ethyl acrylate
n-butyl acrylate
isobutyl acrylate
tert.-butyl acrylate
2-ethylhexyl acrylate
octyl acrylate
lauryl acrylate
myristyl acrylate
2-diethylaminoethyl acrylate
methyl methacrylate
ethyl methacrylate
n-butyl methacrylate
isobutyl methacrylate
tert.-butyl methacrylate
lauryl methacrylate
cyclohexyl methacrylate
allyl methacrylate
2-ethoxyethyl methacrylate
2-dimethylaminoethyl methacrylate
methyl crotonate
ethyl crotonate
1,4-butanediol diacrylate
1,6-hexanediol diacrylate
2-ethyl-2-hydroxymethyl-1,3-propanediol triacrylate
diethylene glycol diacrylate
pentaerythritol triacrylate
pentaerythritol tetraacrylate
ethylene glycol dimethacrylate
1,4-butanediol dimethacrylate
1,6-hexanediol dimethacrylate
diethylene glycol dimethacrylate
triethylene glycol dimethacrylate
tripropylene glycol diacrylate
trimethylolpropane trimethacrylate
2,2,6,6-tetramethylpiperid-4-yl acrylate
2,2,6,6-tetramethylpiperid-4-yl crotonate
2,2,6,6-tetramethylpiperid-4-yl methacrylate Of the compounds VIII, 2,2,4,4-tetramethyl-7-oxa-3,20-diaza-21-oxodispiro[5.1.11.2]heneicosane is particularly preferred and, of the compounds IX, lauryl acrylate.

An aromatic hydrocarbon which is liquid at room temperature, such as, for example, toluene, xylene or mesitylene, is used as a solvent for the process according to the invention. Xylenes (o-, m- and p-) and toluene, in particular o-xylene, are preferred. Mixtures of these aromatic hydrocarbons can also be used.

The catalyst of the formula X is used in an amount of 1 to 10 mol %, relative to a compound of the formula VIII, preferably in an amount of 1 to 5 mol %, in particular in an amount of 2 to 4 mol %. The catalysts of the formula X are the alkali metal salts of the compounds VIII, preferably their lithium salts, sodium salts or potassium salts, in particular sodium salts.

The catalyst is prepared in a known manner by reacting a compound VIII with an alkali metal in an inert solvent, preferably in toluene or xylene. After separating off the solvent, the catalyst can be used as an isolated solid or, without separating off the solvent, in the form of a suspension or a solution.

It is particularly advantageous to use the catalyst "prepared in situ". To this end, an alkali metal is added to the reaction mixture comprising only the solvent and a compound of the formula VIII in an amount of 1 to 10 mol %, relative to the compound VIII, and the compound VIII is reacted to give a catalyst according to the formula X. Only after the alkali metal has completely reacted is a compound of the formula IX added as the second reaction component.

The complete reaction of the alkali metal added with the initially introduced compound VIII is of crucial importance in this case for a high yield of the desired reaction products of the formula I. Complete conversion of the alkali metal is advantageously ensured by heating the mixture comprising solvent, compound VIII and alkali metal for a certain amount of time, depending on the batch size (cf. Ex. 7 and 8) at the reflux temperature. The mixture is then cooled to the actual reaction temperature, and the compound of the formula IX is added.

Thus, without a loss in yield and without longer reaction times compared with the prior art, it is possible in the process according to the invention to dispense with the co-catalyst (phase transfer catalyst) which has a disadvantageous effect on the workup of the reaction mixture.

The compound IX is used in an amount of 1/n to 10/n, preferably 1/n to 3/n, in particular 1/n to 1.5/n mol, relative to 1 mol of the compound VIII. n has the above-mentioned meaning.

The reaction temperature is 30° to 150°, preferably 50° to 120°, in particular 70° to 120, ° C.

The compounds of the formula (I) prepared according to the invention are used in particular as light stabilizers, for example for polyolefins, in particular polyethylene and polypropylene, ethylene/propylene copolymers, polybutylene, and polystyrene, chlorinated polyethylene, and polyvinyl chloride, polyester, polycarbonate, polymethyl methacrylates, polyphenylene oxides, polyamides, polyurethanes, polypropylene oxide, polyacetals, phenol/formaldehyde resins, epoxy resins, polyacrylonitrile and the corresponding copolymers and ABS terpolymers. The compounds prepared according to the invention are preferably used for stabilizing polypropylene, low-molecular-weight and high-molecular-weight polyethylene, ethylene/propylene copolymers, polyvinyl chloride, polyester, polyamide, polyurethanes, polyacrylonitrile, ABS, terpolymers of acrylic ester with styrene and acrylonitrile, copolymers of styrene with acrylonitrile or styrene with butadiene, in particular for polypropylene, polyethylene, ethylene/propylene copolymer or ABS.

The compounds prepared according to the invention can also be used for stabilizing natural substances, for example rubber, and also for lubricating oils. Furthermore, they are also suitable for stabilizing paints.

Suitable paints are any types used in industrial coating, preferably baking enamels, such as are listed in DE 3,149,453.

The compounds prepared according to the invention are incorporated in the materials to be protected by methods known per se, it also being possible to provide monomers or prepolymers or precondensation products with these stabilizers.

Apart from the compounds of the formula (I), further stabilizers can be added to the plastics. Examples of further compounds of this type are antioxidants based on sterically hindered phenols or sulfur- or phosphorus-containing costabilizers or a mixture of suitably sterically hindered phenols with sulfur- and/or phosphorus-containing compounds. Examples of compounds of this type are 2-benzofuranone and/or 2-indolinone compounds, sterically hindered phenols, such as stearyl β-(4-hydroxy-3,5-di-t-butylphenyl) propionate, tetrakis-[methylene-3-(3', 5'-di-t-butyl-4-hydroxyphenyl)-propionoyl]methane, 1,3,3-tris(2-methyl-4-hydroxy-5-t-butylphenyl)butane, 1,3,5-tris(4-t-butyl-3-hydroxy-2,6-dimethylbenzyl)-1,3,5-triazin-2,4,6-(1H, 3H, 5H)trione, bis(4-t-butyl-3-hydroxy-2,6-dimethylbenzyl) dithiol-terephthalate, tris(3,5-di-t-butyl-4-hydroxybenzyl) isocyanurate, triester of β-(4-hydroxy-3,5-di-t-butyl-phenyl) propionic acid with 1,3,4-tris(2-hydroxyethyl)-1,3,5-triazine-2,4,6-(1H, 3H, 5H)trione, glycol bis[3,3-bis(4'-hydroxy-3-t-butylphenyl)butanoate], 1,3,5-trimethyl-2,4,6-tris(3,5-di-t-butyl-4-hydroxybenzyl)benzene, 2,2'-methylenebis(4-methyl-6-t-butylphenyl)terephthalate, 4,4-methylene-bis(2,6-di-t-butylphenol), 4,4'-butylidene bis(t-butyl-meta-kresol), 4,4-thiobis(2-t-butyl-5-methyl-phenol), 2,2'-methylenebis(4-methyl-6-t-butylphenol). Costabilizers which act as antioxidants can also be added such as, for example, sulfur-containing compounds, for example distearyl thiodipropionate, dilauryl thiodipropionate, tetrakis (methylene-3-hexylthiopropionoyl)-methane, tetrakis (methylene-3-dodecylthiopropionoyl)-methane and dioctadecyl disulfide or phosphorus-containing compounds, such as, for example, tris(nonyl-phenyl)phosphite; 4,9-distearyl3,5,8,10-tetraoxadiphosphaspiroundecane, tris(2,4-di-t-butylphenyl) phosphite or tetrakis(2,4-di-t-butylphenyl) -4,4'-biphenylenediphosphonite.

The compounds of the formula I and their abovementioned mixtures can also be used in the presence of further additives. These are known per se and belong, for example, to the group of aminoacrylic compounds, UV absorbers and light stabilizers, such as 2-(2'-hydroxyphenyl)-benzotriazoles, 2-hydroxybenzophenones, 1,3-bis(2'-hydroxybenzoyl)benzenes, salicylates, cinnamic esters, esters of unsubstituted or substituted benzoic acids, sterically hindered amines, oxalamides.

The amount used of the compounds prepared according to the invention of the formula I is 0.01–5% by weight in the case of plastics, 20 to 80% by weight in the case of stabilizer concentrates and 0.02 to 5% by weight in the case of paints.

The examples which follow serve to illustrate the present invention:

COMPARATIVE EXAMPLE A (according to the process of DE 3,524,543)

91.1 g (0.25 mol) of 2,2,4,4-tetramethyl-7-oxa-3,20-diazadispiro[5.1.11.2]heneicosan-21-one in 100 ml of toluene were heated to 80° C. 0.30 g (0.013 mol) of sodium, 1.5 g of triethylbenzylammonium chloride and 76.5 g (0.30 mol) of lauryl acrylate (technical mixture of about 55 to 58% of C12 ester and about 37 to 40% of C14 ester) were then added, and the mixture was stirred at 80° C. for 4 hours. The batch was then stirred three times with 100 ml of water each time, and the solvent was distilled off from the organic phase, giving 168 g of product (slightly yellow highly viscous liquid) having a residual 2,2,4,4-tetramethyl-7-oxa-3,20-diazadispiro-[5.1.11.2]heneicosan-21-one content of 0.7% by weight (by GC).

COMPARATIVE EXAMPLE B

Analogously to Comparative Example A, but using 1.5 g of tetrabutylphosphonium chloride (instead of triethylbenzylammonium chloride).

This gave 167 g of product (slightly yellow highly viscous liquid) having a residual 2,2,4,4-tetramethyl-7-oxa-3,20-diazadispiro[5.1.11.2]heneicosan-21-one content of 1.1% by weight.

EXAMPLE 1

91.1 g (0.25 mol) of 2,2,4,4-tetramethyl-7-oxa-3,20-diazadispiro[5.1.11.2]heneicosan-21-one in 100 ml of toluene were heated to 80° C. 3.0 g (0.008 mol) of the sodium salt of 2,2,4,4-tetramethyl-7-oxa-3,20-diaza-dispiro [5.1.11.2]heneicosan-21-one ("sodium amide") and 76.5 g (0.30 mol) of lauryl acrylate were then added, and the batch was stirred at 80° C. for 4 hours. The mixture was then stirred three times with 100 ml of water each time, and the solvent was distilled off from the organic phase.

This gave 171 g of product (colorless highly viscous liquid) having a residual 2,2,4,4-tetramethyl-7-oxa-3,20-diazadispiro[5.1.11.2]heneicosan-21-one content of 0.9% by weight.

EXAMPLE 2

Analogously to Example 1, except that 5.0 g (0.013 mol) of the sodium salt of 2,2,4,4-tetramethyl-7-oxa-3,20-diazadispiro[5.1.11.2]heneicosan-21-one were used as the catalyst and the batch was stirred at 80° C. for only 2 hours.

This gave 171 g of product (colorless highly viscous liquid) having a residual 2,2,4,4-tetramethyl-7-oxa-3,20-diazadispiro[5.1.11.2]heneicosan-21-one content of 0.9% by weight.

EXAMPLE 3

Analogously to Example 1, except that 1.0 g (0.003 mol) of the sodium salt of 2,2,4,4-tetramethyl-7-oxa-3,20- diazadispiro[5.1.11.2]heneicosan-21-one were used as the catalyst and the batch was stirred at 120° C. for 1.5 hours.

This gave 166 g of product (colorless highly viscous liquid) having a residual 2,2,4,4-tetramethyl-7-oxa-3,20-diazadispiro[5.1.11.2]heneicosan-21-one content of 1.3% by weight.

EXAMPLES 4 to 6

Analogously to Example 1, but using o-xylene instead of toluene as the solvent.

| Catalyst | Final product (g) | Residual 2,2,4,4-tetramethyl-7-oxa-3,20-diazadispiro[5.1.11.2]heneicosan-21-one content in % by weight |
|---|---|---|
| 3.0 g sodium salt | 169 | 0.6 |
| 3.0 g potassium salt | 170 | 0.6 |
| 2.0 g lithium salt | 170 | 0.7 |

EXAMPLE 7

(this example shows the use of a catalyst "prepared in situ")

0.18 g (0.008 mol) of sodium was added to 91.1 g (0.25 mol) of 2,2,4,4-tetramethyl-7-oxa-3,20-diaza-dispiro[5.1.11.2]heneicosan-21-one in 100 ml of o-xylene, and the mixture was heated at reflux until the sodium had been completely converted (about 1 hour). The reaction mixture was then cooled to 80° C., 76.5 g (0.30 mol) of lauryl acrylate were added, and the batch was stirred at 80° C. for 4 hours. The mixture was then stirred three times with 100 ml of water each time, and the solvent was distilled off from the organic phase.

This gave 168 g of product having a residual 2,2,4,4-tetramethyl-7-oxa-3,20-diazadispiro[5.1.11.2]heneicosan-21-one content of 0.4% by weight.

EXAMPLE 8

(Synthesis of the catalyst (sodium salt))

145.6 g (0.40 mol) of 2,2,4,4-tetramethyl-7-oxa-3,20-diazadispiro[5.1.11.2]heneicosan-21-one and 9.2 g (0.40 mol) of sodium were stirred in 500 ml of toluene at the reflux temperature for 24 hours. The batch was then filtered while hot, and the solvent was evaporated from the filtrate, giving 150.9 g (98% of theory) of catalyst as a white solid of melting point 235° C.

What is claimed is:

1. A process for the preparation of 1-oxa-3,8-diaza-4-oxospiro[4.5]decane compounds of the formula I $$\left[\begin{array}{c} H_3C\underset{H_3C}{\overset{CH_2R^2}{\diagup}}\underset{CH_2R^2}{\overset{R^3}{\diagdown}}O\!\!-\!\!\!\underset{}{\overset{}{\diagdown}}\!\!R^4 \\ R^1\!-\!N\quad\quad\quad\quad O \\ \quad\quad\quad\quad N\!-\!CH\!-\!CH\!-\!\overset{\|}{C}\!-\!O\!-\!R^7 \\ \quad\quad\quad\quad\quad\;\; R^5\;\; R^6 \end{array}\right]_n \quad (I)$$

in which n is an integer from 1 to 4,

R$^1$ is hydrogen, C$_1$–C$_4$-alkyl, benzyl, allyl, C$_2$–C$_{30}$-alkanoyl, C$_3$–C$_{20}$-alkenoyl, C$_7$–C$_{11}$-aroyl, C$_8$–C$_{14}$-arylalkanoyl or C$_8$–C$_{20}$-alkylaryl, R$^2$ is hydrogen or C$_1$–C$_4$-alkyl, R$^3$ is hydrogen, C$_1$–C$_{18}$-alkyl, C$_5$–C$_{12}$-cycloalkyl, a phenyl or naphthyl group which can be substituted by chlorine or C$_1$–C$_4$-alkyl, or a C$_7$–C$_{12}$-phenylalkyl group which is unsubstituted or substituted by C$_2$–C$_4$-alkyl, R$^4$ is hydrogen, C$_1$–C$_4$-alkyl, C$_5$–C$_{12}$-cycloalkyl, C$_1$–C$_3$-alkenyl which is substituted by —COOH, carb-C$_1$–C$_4$-alkoxy or carbamoyl, a phenyl, naphthyl or pyridyl group which can be substituted by C$_1$–C$_4$-alkoxy or C$_1$–C$_4$-alkyl, or a C$_7$–C$_{12}$-phenylalkyl group which can be substituted by C$_1$–C$_4$-alkyl, or R$^3$ and R$^4$, together with the carbon atom linking them, are a cycloalkyl group which can be substituted by one to four C$_1$–C$_4$-alkyl groups, or a radical of the formula II $$\underset{H_3C}{\overset{H_3C}{\diagup}}\!\!\underset{CH_2R^2}{\overset{CH_2R^2}{\diagdown}}\!\!N\!-\!R^1, \quad (II)$$

where R$^1$ and R$^2$ have the abovementioned meaning,

R$^5$ is hydrogen, methyl, phenyl or carb-C$_1$–C$_{21}$-alkoxy,

R$^6$ is hydrogen or methyl,

R$^7$ is, if n is 1, hydrogen, C$_1$–C$_{21}$-alkyl, C$_2$–C$_{22}$-alkenyl, C$_7$–C$_{18}$-phenylalkyl, C$_5$–C$_{12}$-cycloalkyl, phenyl, naphthyl, C$_7$–C$_{12}$-alkylphenyl, a radical of the formula $$\underset{CH_3}{\overset{CH_3}{\diagup}}\!\!\underset{CH_2R^2}{\overset{CH_2R^2}{\diagdown}}\!\!N\!-\!R^1,$$

where R$^1$ and R$^2$ have the above meaning, or C$_2$–C$_{20}$-alkyl which is interrupted by $$-O- \quad \text{or} \quad -\underset{R^8}{\overset{|}{N}}-,$$

being hydrogen or C$_1$–C$_{10}$-alkyl,

R$^7$ is, if n is 2, straight-chain or branch C$_1$–C$_{30}$-alkylene, C$_2$–C$_{30}$-alkenylene, phenyldialkylene, these radicals being optionally interrupted by $$-O- \quad \text{or} \quad -\underset{R^8}{\overset{|}{N}}-,$$

where R$^8$ has the above meaning,

R$^7$ is, if n is 3 or 4, a radial of the formula IV, V, VI or VII $$-CH_2-\overset{|}{CH}-CH_2-, \quad (IV)$$

-continued $$\begin{array}{c} | \\ CH_2 \\ | \\ C_2H_5-C-CH_2-, \\ | \\ CH_2 \\ | \end{array} \quad (V)$$

$$\begin{array}{c} -CH_2CH_2-N-CH_2-CH_2-, \\ | \\ CH_2CH_2- \end{array} \quad (VI)$$

$$\begin{array}{c} | \\ CH_2 \\ | \\ -CH_2-C-CH_2-, \\ | \\ CH_2 \\ | \end{array} \quad (VII)$$

which comprises reacting a compound of the formula VIII

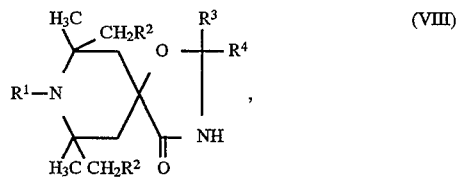

with a compound of the formula IX

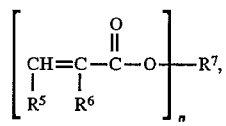

where n, $R^1$, $R^2$, $R^3$, $R^4$, $R^5$, $R^6$ and $R^7$ have the above-mentioned meaning, in an inert solvent at a temperature of 30° to 150° C. in the absence of a phase-transfer catalyst but in the presence of 1 to 10 mol %, relative to the compound VIII, of a catalyst of the formula (X)

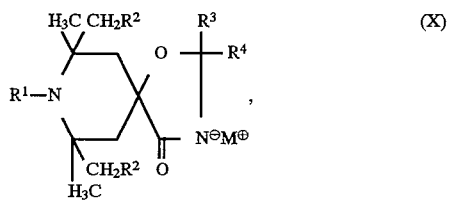

where $R^1$, $R^2$, $R^3$ and $R^4$ have the abovementioned meaning and $M^+$ is an alkali metal cation which has been preformed by reacting a compound of the formula VIII with an alkali metal in an inert solvent over a period from 1 to 24 hours, said inert solvent comprising an aromatic hydrocarbon which is liquid at room temperature.

2. The process as claimed in claim 1, which comprises the steps of:

adding 1 to 10 mol % of an alkali metal to a reaction mixture consisting essentially of a compound of said formula VIII and said inert solvent, said 1 to 10 mol % being in relation to compound of said formula VIII, thereby forming in situ said preformed catalyst of the formula X, and after the alkali metal has completely reacted to form said alkali metal cation, adding a compound of formula IX.

3. The process as claimed in claim 2, wherein the aromatic hydrocarbon is toluene or xylene.

4. The process as claimed in claim 1, wherein said preformed catalyst is a compound of said formula X in which said alkali metal cation is a lithium, sodium, or potassium cation.

5. The process as claimed in claim 1, wherein said pre-formed catalyst is a compound of said formula X in which said alkali metal cation is a sodium cation.

6. The process as claimed in claim 1, wherein the pre-form catalyst is prepared in situ in the reaction mixture before adding the compound of the formula IX.

7. The process as claimed in claim 2, wherein the compound of the formula VIII is 2,2,4,4-tetramethyl-7-oxa-3, 20-diaza-21-oxodispiro[5.1.11.2]heneicosane.

8. The process as claimed in claim 2, wherein the compound of the formula IX is lauryl acrylate.

9. The process as claimed in claim 2, wherein the temperature is 50° to 120° C.

10. The process as claimed in claim 2, wherein the temperature is 70° to 120° C.

11. The process as claimed in claim 2, wherein only one organic phase is employed in or added to the reaction mixture during the whole reaction.

12. The process as claimed in claim 1, wherein said reacting of a compound of said formula VIII with a compound of said formula IX in the presence of said pre-formed catalyst of said formula X is carried out essentially in the absence of a phase-transfer catalyst.

13. The process as claimed in claim 1, wherein said reacting of a compound of said formula VIII with a compound of said formula IX in the presence of said pre-formed catalyst of said formula X is carried out in the absence of any unreacted alkali metal.

14. The process as claimed in claim 2, wherein said alkali metal is lithium, sodium or potassium.

15. The process as claimed in claim 2, wherein said alkali metal is sodium.

* * * * *